(12) United States Patent
Fages et al.

(10) Patent No.: US 7,390,411 B2
(45) Date of Patent: Jun. 24, 2008

(54) METHOD FOR PREPARING A COMPOUND OF INTERACTION OF ACTIVE SUBSTANCES WITH A POROUS SUPPORT USING SUPERCRITICAL FLUID

(75) Inventors: Jacques Fages, Albi (FR); Bernard Freiss, Castres (FR); Christophe Joussot-Dubien, Rochefort du Gard (FR); Jean-Jacques Letourneau, Gragnague (FR); Hubert Lochard, Albi (FR); Florence Marciacq, Orgon (FR); Martial Sauceau, Albi (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 556 days.

(21) Appl. No.: 10/492,346

(22) PCT Filed: Oct. 11, 2002

(86) PCT No.: PCT/FR02/03474

§ 371 (c)(1),
(2), (4) Date: Jan. 19, 2005

(87) PCT Pub. No.: WO03/043604

PCT Pub. Date: May 30, 2003

(65) Prior Publication Data

US 2005/0274671 A1    Dec. 15, 2005

(30) Foreign Application Priority Data

Oct. 12, 2001    (FR)    .................................. 01 13178

(51) Int. Cl.
*B01D 61/00* (2006.01)
*B29B 9/00* (2006.01)

(52) U.S. Cl. ........................... 210/649; 210/634; 264/5; 264/14; 514/58

(58) Field of Classification Search ................. 210/634, 210/639, 649, 650; 264/5–12; 424/489–493, 424/484, 486, 488; 514/58; 428/402; 536/103
See application file for complete search history.

(56) References Cited

U.S. PATENT DOCUMENTS 4,822,497 A    4/1989    Hong et al.

(Continued)

FOREIGN PATENT DOCUMENTS

EP    0706821    4/1996

(Continued)

OTHER PUBLICATIONS

Bertucco et al. Drugs encapsulation using a compressed gs antisolvent technique-Proceedings of the 4th Italian Converence on Supercritical Fluids and thier Applications 1997, 327-334, Ed. E. Reverchon.

(Continued)

*Primary Examiner*—Joseph Drodge
(74) *Attorney, Agent, or Firm*—Blakely, Sokoloff, Taylor & Zafman

(57) ABSTRACT

The invention concerns a method for preparing compounds for interaction of an active substance hardly soluble in an aqueous medium with a porous support. The invention is characterized in that it comprises the following steps: (a) mixing the active substance generated by supercritical fluid and the specific amount of porous support; (b) carrying out a molecular diffusion step by contacting in static mode a supercritical fluid with the mixture obtained at step (a) for the time required to improve the dissolution in the aqueous medium of the mixture obtained at step (a); (c) washing the interactive compound obtained at step (b) with a supercritical fluid flow; (d) recuperating the particles of the interactive compound thus formed. The invention also concerns a compound obtainable by said method.

15 Claims, 4 Drawing Sheets

U.S. PATENT DOCUMENTS

| | | | |
|---|---|---|---|
| 5,043,280 | A | 8/1991 | Fischer et al. |
| 5,389,263 | A | 2/1995 | Gallagher et al. |
| 5,700,482 | A | 12/1997 | Frederiksen et al. |
| 5,990,173 | A | 11/1999 | Patoiseau et al. |
| 6,107,284 | A | 8/2000 | Imbert et al. |
| 6,183,783 | B1 | 2/2001 | Benoit et al. |
| 6,461,642 | B1 * | 10/2002 | Bisrat et al. .................. 424/489 |
| 6,555,139 | B2 * | 4/2003 | Sharma ....................... 424/489 |
| 6,709,595 | B1 | 3/2004 | Perrut et al. |
| 2002/0189454 | A1 | 12/2002 | Perrut |
| 2003/0007990 | A1 * | 1/2003 | Blankenship et al. ........ 424/408 |

FOREIGN PATENT DOCUMENTS

| | | |
|---|---|---|
| EP | 0865819 | 3/1998 |
| EP | 1222009 | 10/2000 |
| GB | 2252059 | 7/1992 |
| GB | 2191715 | 12/1997 |
| JP | 63141559 | 6/1988 |
| WO | WO 89/09639 | 10/1989 |
| WO | WO 95/01221 | 1/1995 |
| WO | WO 97/31691 | 9/1997 |
| WO | WO 98/15348 | 4/1998 |
| WO | WO 99/25322 | 5/1999 |
| WO | WO 99/59710 | 11/1999 |
| WO | WO 00/27844 | 5/2000 |
| WO | WO 02/32462 | 4/2002 |
| WO | WO 02/089851 | 11/2002 |

OTHER PUBLICATIONS

Chou et al., Gas crystallization of polymer-pharmaceutical composite particles, Proceedings of the 4th International Symposium on Supercritical Fluids, 1997, 55-57.

Kim J-H et al., Microencapsulation of Naproxen using Rapid Expansion of Supercritical Solutions, Biotechnol. Prog. 1996, 650-661.

Szu Tu et al., "Applications of dense gases in pharmaceutical processing, Proceedings of the 5th meeting on Supercritical Fluids" 1998, Tome 1, 263-269.

Weber et al Coprecipitation with compressed antisolvents for the manufacture of microcomposites, Proceedings of the 5th meeting on Supercritical Fluids 1998, Tome 1, 243-248.

J. Bleich et al., Production of drug loaded by the use of supercritical gases with the Aerosol Solvent Extraction System (ASES) process, J. Microencapsulation 1996, 13, 131-139.

Tom et al., Applications of supercritical fluids in controlled release of drugs, Supercritical Fluids Engineering Science ACS Symp. Ser. 514, American Chemical Society, Waxhington DC 1992.

Van Hees et al., Application of supercritical carbon dioxide for the preparation of a Piroxicam B-cyclodextrin inclusion compound, Pharmaceutical Research, vol. 16, No. 12, 1999, 1864-1870.

Kamihira M. et al, Formation of inclusion complexes between cyclodextrins and aromatic compounds under pressurized carbon dioxide, J. of Fermentation and Bioengineereing, vol. 69, No. 6, 350-353, 1990.

Szu Tu L. et al. Application of dense gazes in pharmaceutical processing, Proceedings of 5th meeting on supercritical fluids, Nice, France, Mar. 1998.

Jennifer Jung, et al., Particle design using supercritical fluids: literature and patent survey, Journal of Supercritical Fluids 20 (2001) 179-219.

Van Hees et al., Inclusion of piroxicam into B-cyclodextrin by means of supercritical carbon dioxide: thermal, spectroscopic and physiochemical studies, J. Pharm. Belg. 2000, 55.1. vol. 39, 30-31.

Bala Subramaniam et al "Pharmaceutical processing with supercritical carbon dioxide", Journal of Pharmaceutical Science. vol. 86 No. 8, Aug. 1997. 885-889.

"Application of supercritical carbon dioxide for the preparation of a piroxicam-.beta.-cyclodextrin inclusion compound", XP-002203239, Van Hees, Thierry et al, copyright 2002.

"Supercritical carbon dioxide extraction of Podophyllotixin from *Dysosma pleianthum* roots", Y. Choi, et al, XP002203240, copyright 2002.

* cited by examiner

METHOD FOR PREPARING A COMPOUND OF INTERACTION OF ACTIVE SUBSTANCES WITH A POROUS SUPPORT USING SUPERCRITICAL FLUID

The present patent application is a non-provisional application of International Application No. PCT/FR02/03474, filed Oct. 11, 2002.

The present invention relates to a method of interaction of nanoparticulate active substance with a porous support, by the technology of supercritical fluids, in particular that of $CO_2$.

In 40% of cases new pharmaceutical molecules, with high added value, are insoluble or of low solubility in water, which is detrimental to their bioavailability. Increasing the specific surface area of powders allows their dissolution rate to be improved.

The bioavailability of active principles can be considerably enhanced, then, if their dissolution rate is improved.

The generation of fine powders with high specific surface areas by the technology of supercritical fluids has been used for a decade and a half.

Two types of processes are conventionally employed: the RESS (rapid expansion of supercritical solution) process, and the SAS (solvent-antisolvent) process. By modifying the operating conditions it is possible to control the morphology and the size of the particles formed from active substance.

The advantages of using supercritical $CO_2$ as solvent are several:
  possibility of working at low temperature (>31° C.) for active substances sensitive to heat,
  solvency readily modifiable by acting on the parameters of the process (pressure, temperature, flow rate, etc.),
  ready separation of the solvent/solute mixture by simple decompression,
  chemical inertness of the solvent: nontoxic, nonflammable, noncorrosive,
  low cost in comparison with the organic solvents conventionally employed.

Within the pharmaceutical, cosmetics, and nutraceutical fields there exist a number of patents and publications relating to the microencapsulation of an active substance in a coating agent. Nevertheless, the majority of the processes described relate not to the improvement of bioavailability but rather to the adsorption of an active substance on a support.

Bertucco et al. (*Drugs encapsulation using a compressed gas antisolvent technique*—Proceedings of the 4th Italian Conference on Supercritical Fluids and their Applications 1997, 327-334—Ed. E. Reverchon) describe a process in which the active substance is suspended in a solution of biopolymer which acts as the support. This suspension, placed in an autoclave, is subsequently placed in the presence of supercritical $CO_2$ in order to desolvate it (extraction of the solvent by supercritical fluid) and to bring about the complexation of the support by supersaturation on the active substance. This process is a batch process in which the active substance is not precipitated by the supercritical fluid, since it is in suspension. The structure of the particles of active substance is therefore unchanged, which does not contribute to improving its dissolution in an aqueous medium.

An identical process is described by Benoît et al. in their patent application WO 98/13136.

Another technique of deposition of a support consists in dissolving said support in the supercritical fluid and then causing this support to precipitate on the active substance. For this purpose the active substance and its support are placed beforehand in a stirred autoclave and the injection of supercritical $CO_2$ dissolves solely the support (this implies that the support is soluble in the supercritical fluid and the active substance is not), which is precipitated by modifying the pressure and the temperature within the autoclave. In this case the initial structure of the active substance remains unchanged, and it is difficult to control the active substance/support ratio obtained in the precipitated complex. This batch process is detailed in patent application EP 706 821 of Benoît et al.

The microencapsulation process described by Shine and Gelb in their patent application WO 98/15348 consists in:
1. mixing an active substance with an encapsulating polymer,
2. liquefying the polymer by passing in a flow of supercritical fluid,
3. carrying out rapid depressurization so as to solidify the polymer around the active substance.

This process is applicable only with an active substance and a polymer which are insoluble in the supercritical fluid. Consequently the active substance retains its original structure, which does not contribute to improving its bioavailability.

In patent application FR 2 798 863 of Perrut and Majewski, the active substance (kava-kava, curcuma, mixture of black pepper and sweet pepper), extracted beforehand with supercritical fluid, is precipitated in an autoclave containing a porous support. The porous medium studied is maltodextrin. The process is therefore one of simple inclusion in a porous support, without a step of diffusion in static mode of the active substance into its support. However, precipitation on a support is not sufficient to improve substantially the solubility of the active substance in aqueous medium.

The Tomasko group (Chou et al., *GAS crystallization of polymer-pharmaceutical composite particles*, Proceedings of the 4th International Symposium on Supercritical Fluids, 1997, 55-57 and Kim J.-H. et al., *Microencapsulation of Naproxen using Rapid Expansion of Supercritical Solutions*, Biotechnol. Prog. 1996, 12, 650-661) mentions two processes of coprecipitation by RESS and by SAS with supercritical $CO_2$. The active substance studied is naproxen, while the support is poly-L-lactic acid (L-PLA). These two compounds are dissolved simultaneously in acetone before being precipitated by countercurrent injection of $CO_2$, in the case of the SAS process. The complex thus formed is recovered after a wash phase. A mixture of naproxen and L-PLA is placed in a chamber, from which the two compounds are extracted by the supercritical fluid and are precipitated in a second autoclave, as far as the RESS process is concerned. However, the precipitation or coprecipitation of an active substance and a support is not sufficient to improve substantially the solubility of the active substance in aqueous medium. Moreover, there again, no step of molecular diffusion in static mode in order to improve the interpenetration of the active substance with its support is described in these two processes. Finally, the solubility of the active substance in an aqueous medium was not studied.

The same is true of the coprecipitation processes described by Sze Tu et al. (*Applications of dense gases in pharmaceutical processing*, Proceedings of the 5th Meeting on Supercritical Fluids 1998, Tome 1, 263-269), Weber et al., (*Coprecipitation with compressed antisolvents for the manufacture of microcomposites*, Proceedings of the 5th Meeting on Supercritical Fluids 1998, Tome 1, 243-248) and Bleich and Müller (*Production of drug loaded by the use of supercritical gases with the Aerosol Solvent Extraction System (ASES) process*, J. Microencapsulation 1996, 13, 131-139). Subramaniam et al. in their patent application WO 97/31691 developed an apparatus and a process starting from antisolvents which were close to the critical point and were supercritical, which allows particles to be precipitated and coated. The contact phase between the solution, the suspension containing the solute, and the supercritical antisolvent is performed such that it generates high-frequency waves, which divide the solution into a multiplicity of droplets. In this patent the particle size claimed is from 0.1 to 10 μm. Additionally, coating processes are also described. The crystallizations of hydrocortisone, of poly(D,L-lactideglycolide), of ibuprofen, and of camptothecin are described. However, the precipitation or coprecipitation of an active substance and a support is not sufficient to improve substantially the solubility of the active substance in aqueous medium. Furthermore, this process does not describe a step of molecular diffusion in static mode, allowing the bioavailability of the active substance to be improved.

Tom et al. (*Applications of supercritical fluids in controlled release of drugs*, Supercritical Fluids Engineering Science ACS Symp. Ser. 514, American Chemical Society, Washington D.C., 1992) report the first coprecipitation by RESS process of microparticles of lovastatin active substance (anticholesterolemic) complexed to a polymer, DL-PLA. The two compounds are placed in an autoclave, extracted with supercritical $CO_2$, and precipitated in a second chamber. The major drawback of such a process is the active substance/support ratio obtained in the complex. This is because this ratio cannot be selected precisely, since it is determined by the solubility of each of the two compounds in $CO_2$ in the supercritical state. However, the coprecipitation of an active substance and of a support is not sufficient to improve substantially the solubility of the active substance in aqueous medium. Furthermore, this process does not describe a step of molecular diffusion in static mode, allowing the bioavailability of the active substance to be improved and, moreover, its solubility in an aqueous medium is not studied.

A process for impregnating pharmaceutical actives is claimed in patent application WO 99/25322 of Carli et al. It breaks down as follows:
1. dissolution of the active principle by RESS process,
2. contacting of the supercritical fluid containing the active principle with the crosslinked polymer,
3. impregnation of the crosslinked polymer in static or dynamic mode,
4. removal of the supercritical fluid.

Only active substances which are soluble in the supercritical fluid can be compared by this process, since the first step consists in extracting the active principle with the supercritical fluid. Moreover, the process is not an inclusion process but a process of impregnation on a support, and no result is given concerning the improvement of the dissolution in an aqueous medium of the active principle thus prepared. Finally, the impregnated polymer does not undergo a step of washing with supercritical fluid.

Fisher and Müller describe in their patent U.S. Pat. No. 5,043,280 a process for preparing active substances on a support with supercritical fluid. This process consists in contacting one or more actives with one or more supports in supercritical medium. For this purpose the actives and the supports are either precipitated or coprecipitated by SAS and/or RESS processes. The compounds are obtained in sterile form. However, the precipitation or coprecipitation of an active substance and a support is not sufficient to improve substantially the solubility of the active substance in aqueous medium. Furthermore, this process does not describe a step of molecular diffusion in static mode, allowing the bioavailability of the active substance to be improved, and, moreover, its solubility in an aqueous medium is not studied.

Van Hees et al. (*Application of supercritical carbon dioxide for the preparation of a Piroxicam-β-cyclodextrin inclusion compound*, Pharmaceutical Research, Vol. 16, No. 12, 1999) describe in their publication a process for including piroxicam in β-cyclodextrins using supercritical $CO_2$. The process consists in placing a mixture of piroxicam and β-cyclodextrins (molar ratio 1/2.5) in a pressurized autoclave, which is left in static mode. Following depressurization, the mixture obtained is ground and homogenized before characterization.

These analyses allow conclusions to be drawn concerning the degree of complexation of the piroxicam with the β-cyclodextrin, but do not provide any result concerning the improvement of the dissolution in aqueous medium of the piroxicam/β-cyclodextrin complex in relation to piroxicam alone. Moreover, the active substance used was not generated by supercritical fluid, and no step of washing the complex with supercritical fluid is performed.

Kamihira M. et al. (*Formation of inclusion complexes between cyclodextrins and aromatic compounds under pressurized carbon dioxide*, J. of Fermentation and Bioengineering, Vol. 69, No. 6, 350-353, 1990) describe a process for extracting volatile aromatic compounds and for trapping them by inclusion in cyclodextrins. Geraniol and mustard oil are extracted in this way by a RESS process and are vaporized in dynamic mode in a second autoclave containing a mixture of cyclodextrin and water. The influence of the parameters of temperature, pressure, and water content is studied by measuring the level of inclusion of the active substances in the cyclodextrins. The inclusion step described in this publication is performed in dynamic and not static mode as claimed in the present invention. Moreover, this process does not include a step of washing of supercritical fluid. Finally, the solubility of the active substance in an aqueous medium is not studied.

Sze Tu L. et al. (*Application of dense gases in pharmaceutical processing*, Proceedings of $5^{th}$ meeting on supercritical fluids, Nice, France, March 1998) describe in their publication how to perform precipitation by SAS of an active substance (para-hydrobenzoic acid) and polymers (PLGA—polylactictide-co-glycolide—or PLA—poly-L-lactic acid). This coprecipitation is performed by two techniques; either with the polymer and the active substance in two different solutions; or else in the same solution. In both cases the two solutions, or the solution, containing the two components are treated by supercritical $CO_2$ SAS. However, the coprecipitation of an active substance and a porous support is not sufficient to improve substantially the solubility of the active substance in aqueous medium. Moreover, this method does not describe a step of molecular diffusion in static mode, allowing the bioavailability of the active substance to be improved, and, moreover, its solubility in an aqueous medium is not studied.

The same is true of the coprecipitation processes described by Jung et al. in their patent FR 2 815 540. This is a process for fabricating very fine particles containing at least one active principle inserted into a host molecule, and also a device allowing this process to be implemented. This process consists in dissolving the active principle in a first liquid solvent, and a product formed from host molecules, of cyclodextrin or crown ether type, in a second liquid solvent. The solutions are subsequently contacted with a fluid at supercritical pressure, so as to cause the molecules to precipitate, in an SAS process. The components, as in the process described by Sze Tu L. in the article cited before, can be dissolved in the same solvent. The results presented by Jung et al. do not claim any improvement in the dissolution rate. However, the coprecipitation of an active substance and a support of cyclodextrin type is not sufficient to improve substantially the solubility of the active substance in aqueous medium. Furthermore, this method does not describe a step of molecular diffusion in static mode, allowing the bioavailability of the active substance to be improved, and, moreover, its solubility in an aqueous medium is not studied.

The inventors of the present specification have discovered, surprisingly, that a method comprising the steps of generating an active substance of low solubility in an aqueous medium by a supercritical fluid, mixing it with a porous support, followed by a step of molecular diffusion by the supercritical fluid in static mode and of washing with the supercritical fluid, makes it possible to prepare an interaction compound by very greatly increasing the solubility of the active substance in an aqueous medium, and hence its bioavailability.

Indeed, the step of inclusion in static mode coupled with the phase of precipitation of the active substance to its support has made it possible, surprisingly, to improve the dissolution of the active substance in aqueous medium. Moreover, the third phase of washing in a supercritical medium, which consists in eliminating the residual solvents by passage of a flow of supercritical $CO_2$, also makes it possible, surprisingly, besides the washing of the interaction compound, to increase the dissolution following this step.

Moreover, these steps can be carried out batchwise or continuously, as is the case in particular for the diffusion and the washing. This makes it possible, therefore, to lighten the method relative to the conventional steps, which would be:
1. crystallization
2. solid/liquid separation
3. drying
4. inclusion in the support
5. micronization The present invention accordingly provides a method for preparing a compound of interaction of an active substance of low solubility in an aqueous medium with a porous support, characterized in that it comprises the following steps:
(a) mixing, advantageously intimately, the active substance generated by supercritical fluid and the defined amount of porous support,
(b) implementing a step of molecular diffusion by contacting in static mode a supercritical fluid with the mixture obtained in step (a) for the time required to improve the dissolution in an aqueous medium of the mixture obtained in step (a),
(c) washing the interaction compound obtained in step (b) with a flow of supercritical fluid,
(d) recovering the particles of the interaction compound thus formed.

An active substance of low solubility in an aqueous medium is for the purposes of the present invention any active substance which is of low solubility or is insoluble in an aqueous medium and which has in particular a solubility of less than at least 20 μg/ml. In particular it may be a pharmaceutical, cosmetic or nutraceutical active. Advantageously it is an active substance selected from the group consisting of anilide derivatives, epipodophyllotoxin derivatives, piroxicam, valeric acid, octanoic acid, lauric acid, and stearic acid. In the case of the anilide derivatives it is advantageously a derivative of general formula I below:

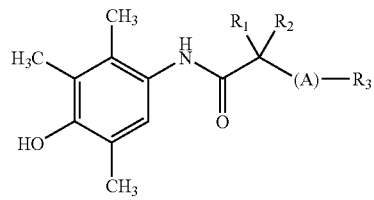

in which:

$R_1$ and $R_2$, which are identical or different, represent independently of one another a hydrogen atom; a linear or branched $C_1$-$C_6$ alkyl radical; an aromatic group such as phenyl, naphtyl or pyridyl which is optionally substituted by one or more $C_1$-$C_4$ alkyl, $C_1$-$C_4$ alkoxy, hydroxyl or halo groups, $R_3$ represents a linear or branched $C_6$-$C_{15}$ alkyl chain or a phenyl group which is optionally substituted by one or more $C_1$-$C_4$ alkyl, $C_1$-$C_4$ alkoxy, hydroxyl or halo groups, A represents a sulfur or oxygen atom or the sulfoxy group.

More advantageously still the substance is (S)-2',3',5'-trimethyl-4'-hydroxy-α-dodecylthiophenyl-acetanilide (F12511). Since the compounds of formula I can possess centers of asymmetry, the active substance according to the present invention may be one of the various stereoisomers or enantiomers or a mixture thereof. These derivatives and the way in which they are prepared are described in patent application FR 2 741 619.

In the case of the epipodophyllotoxin derivatives, the substance is advantageously a derivative of general formula II below

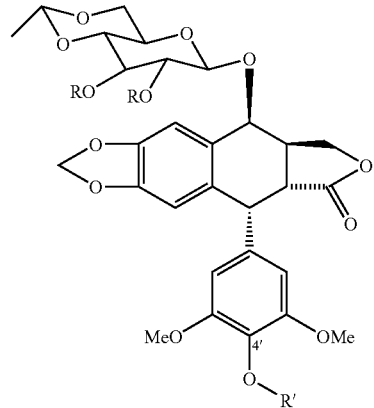

in which R' represents a hydrogen atom; a monoester phosphate group; a carbamate group of type —CO—N($R_1R_2$) in which N($R_1R_2$) represents aminodiacetic groups and a polycyclic amine such as 3-aminoquinuclidine; an acyl group of phosphonoacetic type $H_2O_3P$—$CH_2$—CO or a radical R, R represents an acyl group of formula A-Z-$CH_2$—CO in which Z represents an oxygen or sulfur atom, an $SO_2$ group, a linear or branched $C_{1-4}$ alkylene, in this case A represents a substituted or unsubstituted substituted phenyl nucleus, on condition that where R=R', in other words triacyl derivatives, A represents an aromatic nucleus which possesses a salifiable function, where R'≠R, A represents a benzyl, naphtyl, or heteroaryl radical or substituted or unsubstituted phenyl radical, it being possible in this case for the phenyl to be substituted one or more times, irrespective of its position on the aromatic nucleus, by groups such as halogens, F, Cl, Br, linear or cyclic $C_{1-6}$ alkoxy, $C_{1-6}$ alkyl, methylenedioxy, $OCF_3$, $CF_3$, $NO_2$, CN, $OCH_2$ aryl, OH, $OPO_3H_2$, $CH_2PO_3H_2$, $PO_3H_2$, $OCH_2CO_2H$, COOH, $CH_2COOH$, $COCH_3$, CHO, A-Z may also represent an $OCH_2CO_2H$, $SO_2CH_2COOH$ or $PO_3H_2$ group.

More advantageously still the substance is 4'-demethyl-4'-deoxy-4'-phosphate-4-O-(2,3-bis-(2,3,4,5,6-penta-fluorophenoxyacetyl)-4,6-ethylidene-β-D-glucosyl)-epipodophyllotoxin (L0081).

These derivatives and the way in which they are prepared are described in patent application FR 2 725 990.

An active substance generated by supercritical fluid is for the purposes of the present invention any active substance as defined above which has undergone a step of generation by supercritical fluid, in other words a step allowing its specific surface area to be increased by virtue of the use of the supercritical fluid. Such a step advantageously consists in an RESS or SAS process.

A porous support is for the purposes of the present invention any appropriate porous support which is soluble in an aqueous medium. The porous support is advantageously selected from the group consisting of cyclodextrins and a mixture thereof. Advantageously the support is γ-cyclodextrin.

A supercritical fluid is for the purposes of the present invention any fluid which is used at a temperature and a pressure greater than their critical value. Advantageously the fluid is $CO_2$.

By "static mode" is meant in the sense of the present invention a reaction or a method in which all of the reactants are combined simultaneously and the reaction is left to proceed. For example, in step (b) of the present invention, a cocrystallized powder, water, and supercritical $CO_2$ are placed in an autoclave and left to react for 16 hours. The mass of product does not change during the reaction.

Conversely, in dynamic mode, the reactants are supplied in accordance with the progress of the reaction or of production. In a dynamic mode there is often circulation of a fluid or stirring. The mass of product changes during production. In the method of the present invention step (a) is typically a dynamic phase.

An intimate mixture is for the purposes of the present invention a mixture of A and B in which A and B are uniformly distributed within the mixture obtained.

In one particular embodiment the method according to the present invention is such that the porous support is generated by supercritical fluid and such that step (a) comprises the following steps:

(a1) dissolving the active substance and the porous support in an organic solvent, said organic solvent being soluble in the supercritical fluid, (a2) continuously contacting the solution obtained in step (a1) with said supercritical fluid, so as to effect controlled desolvation of the active substance and the support, and to ensure their coacervation, (a3) washing the complex thus formed by extracting the residual solvent using the supercritical fluid, then separating the solvent in the liquid state and the supercritical fluid in the gaseous state.

Advantageously step (a) consists in a coprecipitation of the active substance and of the porous support by the SAS process.

In another embodiment the method according to the present invention is such that the active substance, before being used in step (a), is generated by the process comprising the following steps:

(i) dissolving the active substance in an organic solvent, said organic solvent being soluble in the supercritical fluid, (ii) continuously contacting the solution obtained in step (i) with said supercritical fluid, so as to effect desolvation of the active substance, and to ensure its coacervation, (iii) washing the particles of active substance thus formed by extracting the residual solvent using said supercritical fluid, then separating the solvent in the liquid state and the supercritical fluid in the gaseous state, and such that the porous support used in step (a) is in solid form.

Advantageously the active substance, before being used in step (a), is generated by precipitation in accordance with the SAS process.

In a third embodiment the method according to the present invention is such that the active substance, before being used in step (a), is generated by the process comprising the following steps:

(i) extracting the active substance with the supercritical fluid, optionally admixed with a cosolvent, (ii) vaporizing the supercritical mixture so as to effect desolvation of the active substance, and to ensure its coacervation, (iii) washing the particles of active substance thus formed with the supercritical fluid, then optionally separating the cosolvent in the liquid state and the supercritical fluid in the gaseous state, and such that the porous support used in step (a) is in solid form.

Advantageously the active substance, before being used in step (a), is generated by precipitation in accordance with the RESS process.

In a fourth embodiment the method according to the present invention is such that step (a) comprises the following steps:

(a1) dissolving the active substance in an organic solvent, said organic solvent being soluble in the supercritical fluid, (a2) continuously contacting the solution thus obtained with the supercritical fluid, so as to effect desolvation of the active substance, and to ensure its coacervation on the porous support placed in the reactor beforehand, (a3) washing the complex thus formed by extracting the residual solvent using the supercritical fluid, then separating the solvent in the liquid state and the supercritical fluid in the gaseous state.

Advantageously step (a) consists in the precipitation of the active substance on the porous support by the SAS process.

In a fifth embodiment the method according to the present invention is such that step (a) comprises the following steps:

(a1) extracting the active substance with a supercritical fluid, optionally admixed with a cosolvent, (a2) vaporizing the supercritical mixture so as to effect desolvation of the active substance, and to ensure its coacervation on the porous support placed in the reactor beforehand, (a3) washing the complex thus formed with the supercritical fluid, then optionally separating the cosolvent in the liquid state and the supercritical fluid in the gaseous state.

Advantageously step (a) consists in the precipitation of the active substance on the porous support by the RESS process.

Advantageously the organic solvent or the cosolvent is selected from the group consisting of alcohols, in particular methanol or butanol, ketones, in particular acetone, methyl ethyl ketone, cyclohexanone or N-methylpyrrolidone, acetic acid, ethyl acetate, dichloromethane, acetonitrile, dimethylformamide, dimethyl sulfoxide (DMSO), and a mixture thereof. Advantageously the solvent or cosolvent is ethanol or dimethyl sulfoxide.

Advantageously step (b) of molecular diffusion of the method according to the present invention is performed with stirring.

More advantageously still step (b) of molecular diffusion of the method according to the present invention is performed in the presence of a diffusion agent.

A diffusion agent is for the purposes of the present invention any solvent which promotes interaction of the active substance with the support.

Advantageously this diffusion agent is selected from the group consisting of alcohol, water with or without surfactant, and mixtures thereof. More advantageously still the agent is water.

This diffusion agent may be added continuously or discontinuously.

The time required for the molecular diffusion of step (b) is determined by any appropriate method. This step (b) may be repeated as many times as desired in order to obtain a satisfactory dissolution rate.

Advantageously step (b) lasts approximately 16 hours. The pressure and temperature conditions of step (b) are selected so as to promote molecular diffusion. Advantageously the pressure of the supercritical fluid is between 10 MPa and 40 MPa and the temperature is between 0 and 120° C.

More advantageously still the supercritical fluid is used at a pressure of between 10 MPa and 40 MPa and at a temperature of between 0 and 120° C. in all the steps of the method according to the present invention.

Each of the steps of the method according to the present invention is advantageously implemented in a closed reactor, in particular an autoclave.

Advantageously the method according to the present invention is performed continuously.

The present invention likewise provides a compound of interaction of an active substance of low solubility in an aqueous medium with a porous support, characterized in that it is obtainable by the method according to the present invention.

Advantageously the interaction compound according to the present invention is such that the active substance thus complexed has a solubility in 5% aqueous sodium lauryl sulfate solution of greater than approximately 600 µg/ml.

Physical Characteristics of the Powders in the Various Steps:

Active Principle Powder Obtained by RESS:
    extremely light and pulverulent powder,
    size and type of monodisperse crystals: rodlets with a length of 1-3 µm and a diameter of 100 to 200 nm,
    bulk density of 12 kg/m$^3$.

Active Principle Powder Obtained by SAS:
    very light and pulverulent powder,
    size and type of monodiperse crystals: rodlets with a length of 10-20 µm and a diameter of 100 nm,
    bulk density of 97 kg/m$^3$.

Cocrystallized Powder (Active Principle/Cyclodextrin)
    fine, light and pulverulent powder,
    bulk density 176 kg/m$^3$ Cocrystallized Powder, Aged (Active Principle/Cyclodextrin)
    dense and nonpulverulent powder,
    bulk density 639 kg/m$^3$.

Other subjects and advantages of the invention will become apparent for the skilled worker from the detailed description below and by means of references to the illustrative drawings which follow.

The method according to the invention includes in particular a step of molecular diffusion in supercritical medium, which allows a high level of interaction of the particles of active substance in the envisioned support, as shown by the photos taken with the scanning electron microscope (FIGS. 1 to 6). In these photos it can be seen that the structure of the compound is totally modified during the diffusion. Moreover, the dissolution in aqueous medium is also modified.

Figure 1:
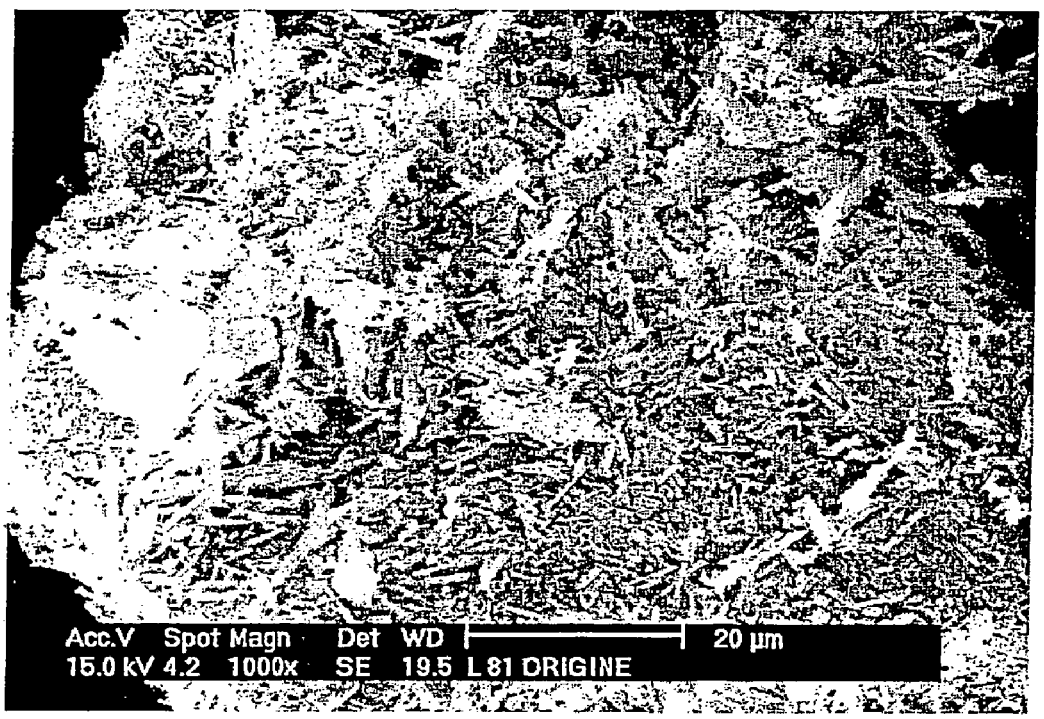
FIG. 1 represents an SEM photo with an enlargement of 1000× of the product F12511 obtained after crystallization and drying by conventional means.
Figure 2:
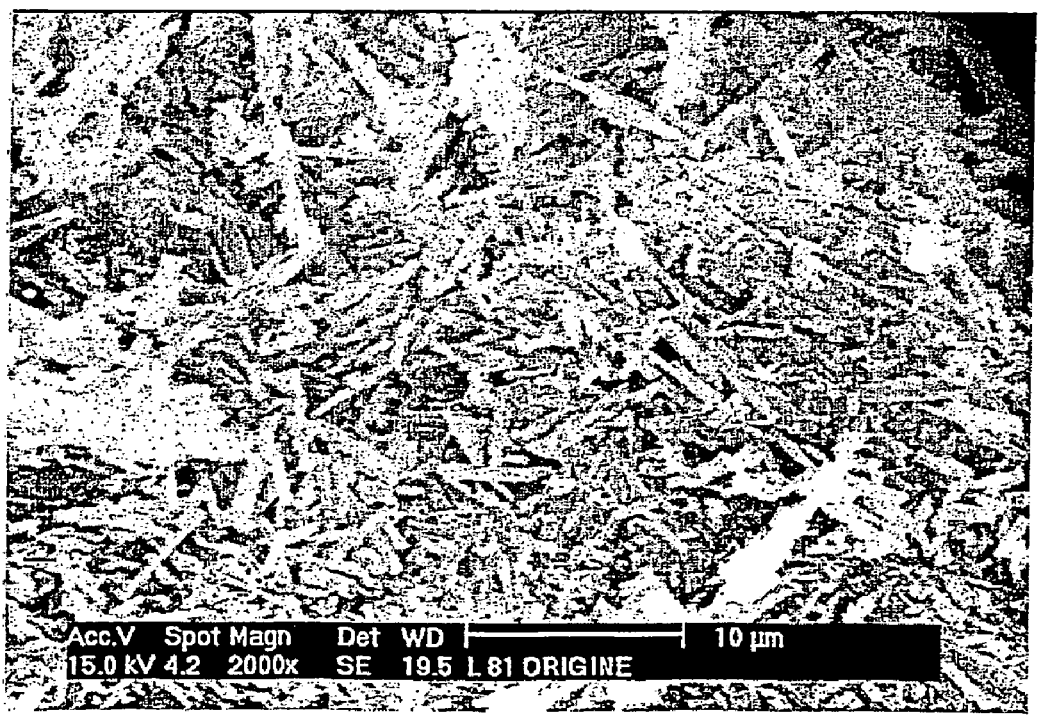
FIG. 2 represents an SEM photo with an enlargement of 2000× of the product F12511 obtained after crystalliztion and drying by conventional means.

Accordingly the compound according to FIGS. 1 and 2 has a solubility after 2 hours of 6 µg/ml in 5% aqueous sodium lauryl sulfate solution.

Figure 3:
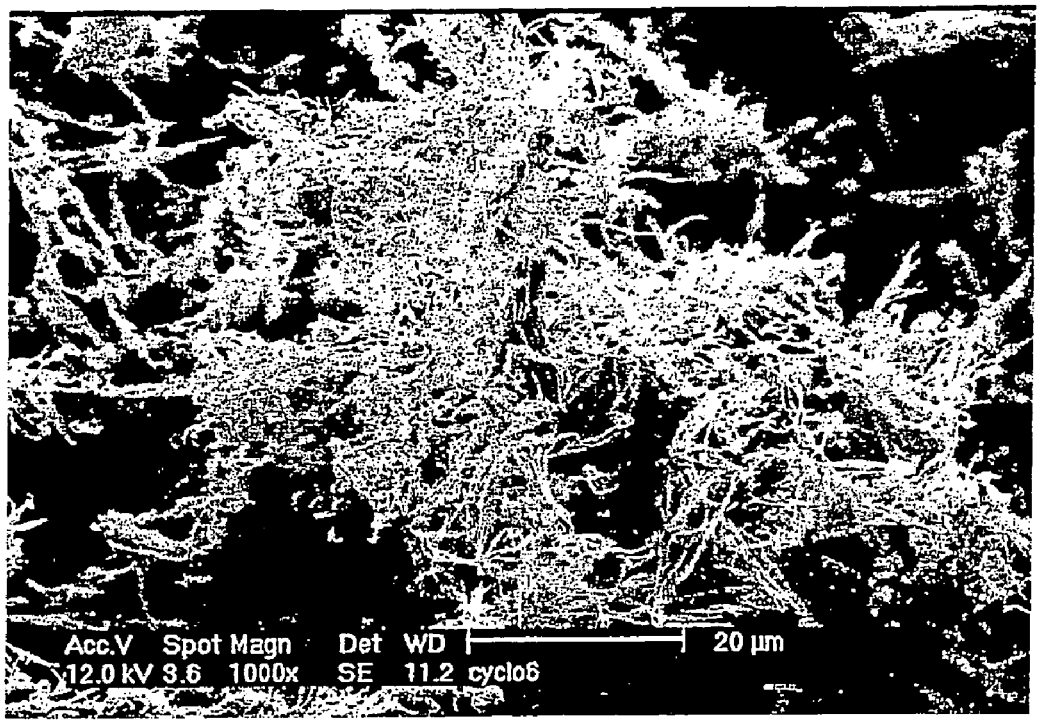
FIG. 3 represents an SEM photo with an enlargement of 1000× of the complex obtained after coprecipitation by the SAS process and washing with supercritical $CO_2$ of a solution of the product F12511 and γ-cyclodextrin in DMSO.
Figure 4:
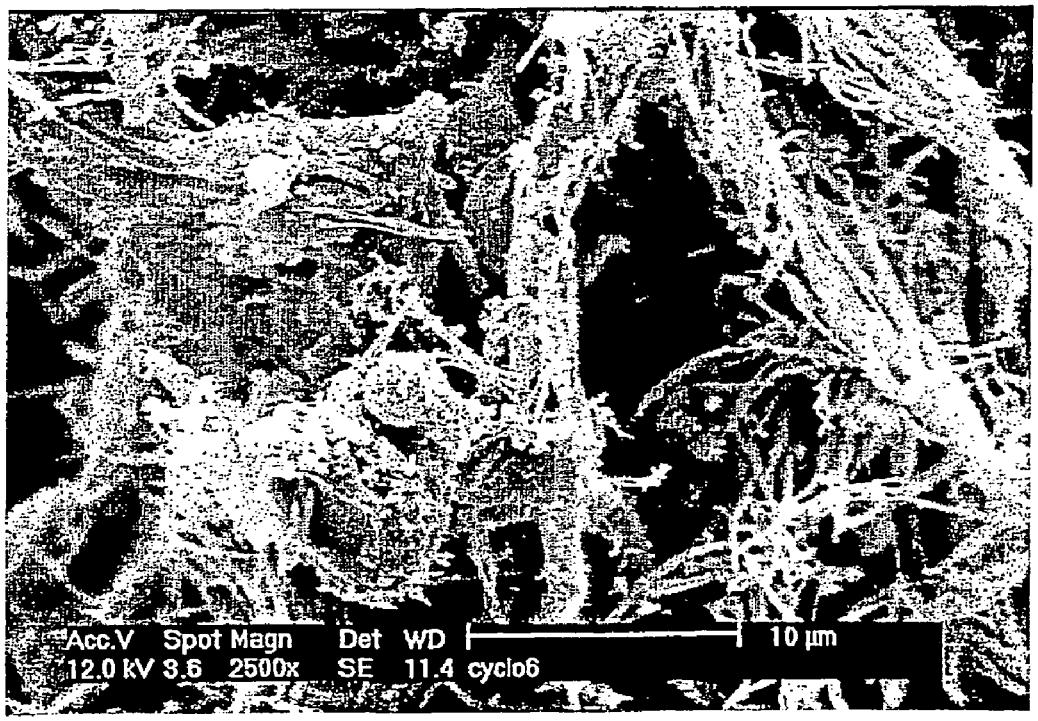
FIG. 4 represents an SEM photo with an enlargement of 2000× of the complex obtained after coprecipitation by the SAS process and washing with supercritical $CO_2$ of a solution of the product F12511 and γ-cyclodextrin in DMSO.

The complex according to FIGS. 3 and 4 has a solubility after 2 hours of 86 µg/ml in 5% aqueous sodium lauryl sulfate solution.

Figure 5:
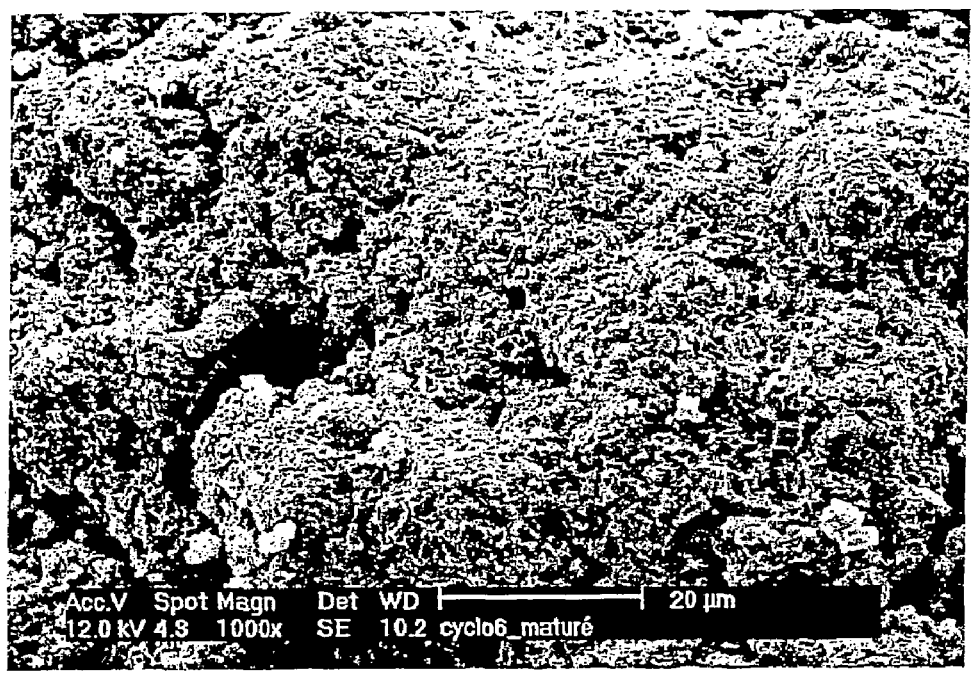
FIG. 5 shows an SEM photo with an enlargement of 1000× of the same complex as FIGS. 3 and 4 after 16 hours of molecular diffusion in supercritical medium, in the presence of water.
Figure 6:
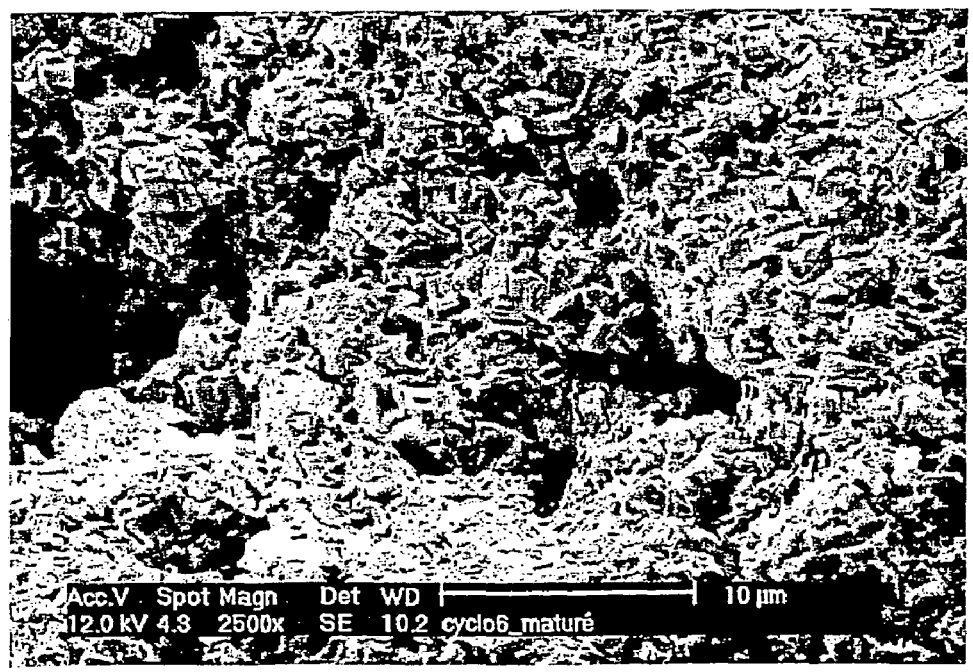
FIG. 6 shows an SEM photo with an enlargement of 2000× of the same complex as FIGS. 3 and 4 after 16 hours of molecular diffusion in supercritical medium, in the presence of water.

The complex according to FIGS. 5 and 6 has a solubility after 2 hours of 516 µg/ml in 5% aqueous sodium lauryl sulfate solution.

The objective during this diffusion step is to improve the dissolution of the microparticles of active substance.

The following step, which is a step of washing with supercritical fluid, further makes it possible to enhance the dissolution rate of the compound of interaction of the active substance in the porous support.

Dissolution after two hours in aqueous medium is multiplied by approximately 100 by the method according to the present invention.

The examples which follow of how the method is implemented are given by way of indication and not limitation.

Powder Analysis Protocols

Dissolution Tests on Product F12511

Operating Conditions:

Spectrophotometric detector set at 220 nm.

C8 graft column (Lichrospher 60RP-Select B), dimensions 25×0.4 cm, particle size: 5 µm.

Mobile Phase:

|  |  |
|---|---|
| Acetonitile | 820 ml |
| Purified water | 180 ml |
| Glacial acetic acid | 1 ml |

Flow Rate: 1 ml/min

Preparation of Solutions:

Solution Under Examination

Introduce an amount of complex corresponding to approximately 100 mg of product F12511 into 100 ml of 5% (m/V) sodium lauryl sulfate in $H_2O$. Subject the system to magnetic stirring in a waterbath at 37° C.±0.5° C. Withdraw 2 ml sample of this suspension after 2 hours of stirring and filter it on a Gelman GHP Acrodisc GF (R) filter.

Dilute the samples 1/5 in the mobile phase. Carry out 2 tests.

Control Solution

Introduce 8 mg of reference product F12511 (starting material used to prepare the complex) in a 100 ml flask and dissolve it in 1 ml of tetrahydrofuran (THF). Make up to volume with the mobile phase.

|  | Range | | | | |
|---|---|---|---|---|---|
|  | T1 | T2 | T3 | T4 | T5 |
| Control solution (ml) | 0.5 | 1.5 | 2.0 | 3.0 | 4.0 |
| Mobile phase |  |  | qs 20 ml |  |  |
| Concentration (µg/ml) | 2.0 | 6.0 | 8.0 | 12.0 | 16.0 |

Test Procedure:

Inject 20 µl of each control solution. Measure the area of the peak of product F12511 and represent its variation as a function of concentration in the form of a graph. The correlation coefficient is>0.995. Inject 20 µl of the test solution. Measure the area of the peak of product F12511 present in the test solution, and ensure that it lies between that of T1 and of T5 in the range.

If this is not the case, perform a dilution in the solubilizing solvent and/or adjust the injection volume of the test solution.

From this, work out the concentration X (µg/ml) of the test solution.

Calculate the amount of dissolved product F12511 in mg/ml by the following formula:

$$\frac{X \times 20 \times F \times 5}{1000 \times Y}$$

Y: injection volume of the test solution

F: dilution factor

Measurements of Specific Surface Areas

The specific surface area measurements were carried out on a BET ASAP 2010 adsorption apparatus from Micrometrics.

Sample Preparation

Before the measuring phase, the sample requires a degassing step. This step consists in evacuating the cell containing the sample until a vacuum of at least 0.003 mm Hg, or approximately 0.004 mbar, is reached stably. This degassing is carried out at a temperature of 50° C. (duration: approximately 16 hours).

At the end of degassing, the cell containing the sample is filled with helium and transferred to the measuring station, where evacuation is repeated before analysis.

Processing of the Adsorption Isotherms

The specific surface area was determined in accordance with the BET theory, i.e., in accordance with the following relationship:

$$\frac{1}{W \cdot [(P_0/P) - 1]} = \frac{1}{CWm} + \frac{C-1}{Wm \cdot C} \cdot (P/P_0)$$

W: volume of gas adsorbed (under standard temperature and pressure (STP) conditions) per unit mass of sample.

Wm: volume of gas adsorbed (under STP conditions) in a monolayer per unit mass of sample.

$P_0$: saturation pressure.

C: constant.

The isotherm is then plotted as follows:

$$\frac{1}{W \cdot [(P_0/P) - 1]}$$

As a function of $P/P_0$: we then have a straight line of which the slope and the ordinate at the origin give us C and Wm.

The specific surface area is then given by the following formula:

$$a(m^2 \cdot g^{-1}) = N_m N_A E$$

E: space occupancy of the nitrogen molecule. For nitrogen at 77 K operating temperature this is generally taken to be $E = 0.162 \text{ nm}^2$.

$N_A$: Avogadro's number.

$N_m$: number of moles of nitrogen adsorbed on a monolayer per unit mass of sample, calculated from Wm. The measurements are carried out within a conventional field of relative pressure in which the BET theory is valid, namely $0.05 < P/P_0 < 0.2$. In order to verify the validity of this theory, one practical means is to look at the direction in which the quantity $N_{adsorbed} \cdot (1-P/P_0)$ changes as a function of $P/P_0$: it should increase continually with $P/P_0$.

Verify the range of applicability of the BET theory in this way, and if necessary readjust the range of relative pressures.

COMPARATIVE EXAMPLE 1

Precipitation by SAS/DMSO of Product F12511

A 150 ml solution of the product F12511 in DMSO with a concentration of 115 g/l is precipitated continuously by the solvent-antisolvent (SAS) process, in the presence of $CO_2$, in a 2 l autoclave equipped with a 1.37 l basket. The flow rate of the solvent pump is 0.6 ml/min. The temperature and pressure within the autoclave are selected so as to give a $CO_2$ density of 0.8. After approximately 130 ml of solution have been precipitated the injection of the solute and then the injection of $CO_2$ are stopped, and washing is carried out by passage of a flow of $CO_2$ (300 bar, 50° C.) for 3 hours. The autoclave is subsequently depressurized. The yield of this step is 87%.

| Nature of powder | Dissolution (µg/ml) | BET (m²/g) |
|---|---|---|
| F12511 | 6-12 | 14 |
| F12511 precipitated by SAS | 62 | 54 |

COMPARATIVE EXAMPLE 2

Precipitation by RESS of Product F12511

10 g of product F12511 are placed in an autoclave and extracted with supercritical $CO_2$ at 100° C. and 265 bar. The fluid is then precipitated in a second chamber, and 0.6 g of product F12511 is recovered. Measurements are made of the dissolution after two hours and of the specific surface area:

| Nature of powder | Dissolution (µg/ml) | BET (m²/g) |
|---|---|---|
| F12511 | 12 | 14 |
| F12511 precipitated by RESS | 76 | 67 |

COMPARATIVE EXAMPLE 3

Coprecipitation of Product F12511 and γ-cyclodextrin by SAS/DMSO

A 150 ml solution of product F12511 (concentration: 57.5 g/l) and γ-cyclodextrin (concentration of 172.5 g/l) in DMSO is precipitated continuously by the solvent-antisolvent (SAS) process, in the presence of $CO_2$, in a 2 l autoclave equipped with a 1.37 l basket. The flow rate of the solvent pump is 0.4 ml/min. The temperature and pressure within the autoclave are selected so as to give a $CO_2$ density of 0.9. After approximately 100 ml of solution have been precipitated, the injection of the solute and then the injection of $CO_2$ are stopped, and the powder obtained is washed by passage of a flow of $CO_2$ (300 bar, 50° C.) for 2 hours. The autoclave is subsequently depressurized.

The yield of this step is 81%.

The results of the dissolution measurements are collated in the table below:

| Nature of powder | Dissolution (µg/ml) |
|---|---|
| F12511 | 12 |
| F12511 coprecipitated by SAS/DMSO | 100 |

EXAMPLE 4

Coprecipitation, Inclusion, and Washing Starting from a Solution of Product F12511 and γ-cyclodextrin in DMSO A 450 ml solution of product F12511 (concentration: 40 g/l) and γ-cyclodextrin (concentration of 240 g/l) in DMSO is precipitated continuously with a solvent-antisolvent (SAS) process, in the presence of $CO_2$, in a 6 l autoclave equipped with 4 l basket. The flow rate of the solvent pump is 1.1 ml/min. The temperature and pressure within the autoclave are selected so as to give a $CO_2$ density of 0.9±0.05. After approximately 450 ml of solution have been precipitated, the injection of the solute and the injection of $CO_2$ are stopped, and the system is let down gently, so as not to liquefy the supercritical fluid.

The average yield of this step is 94%.

The powder coprecipitated in the preceding step is mixed with osmosed water (mass ratio of 25% of water), and the mixture is placed in the 4 L Poral basket, which in turn is placed in the 6 l precipitation autoclave.

The autoclave is closed and the system is pressurized with supercritical $CO_2$ so as to give a static pressure of 300 bar, and a temperature of 65° C. within the autoclave.

After one night of molecular diffusion the autoclave is let down gently, and this step is repeated, without adding diffusion agent (water), for one night.

The complex thus obtained is then washed with a flow of supercritical $CO_2$ (270 bar, 40° C.) for 8 hours. Letdown is followed by a dissolution measurement on the resulting powder.

| Nature of powder | Dissolution (µg/ml) |
|---|---|
| F12511 before coprecipitation | ~15 |
| F12511/γ-cyclodextrin compound after molecular diffusion | 440 |
| F12511/γ-cyclodextrin compound after molecular diffusion, and washed | 662 |

These results show the advantage of a method combining coprecipitation, inclusion, and washing in super-critical medium for improving the dissolution of the active principle in aqueous medium.

Figure 7:
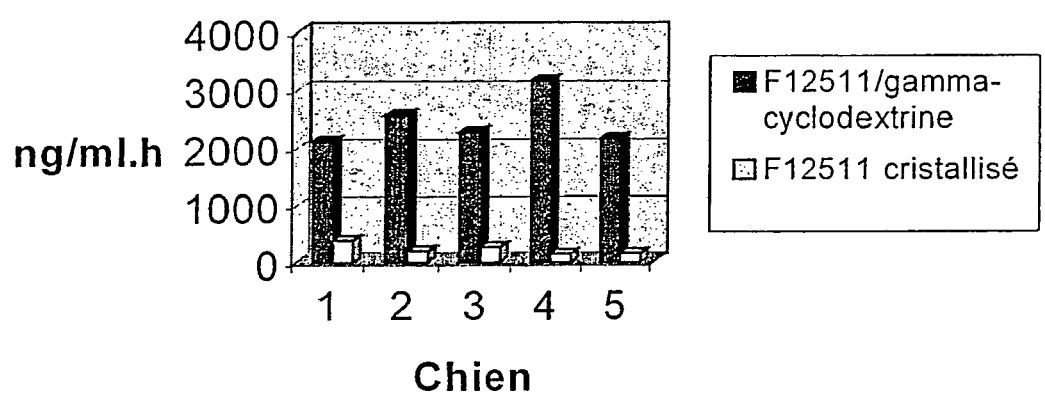
FIG. 7 shows a histogram of the bioavailability of the product F12511 according to the formulation used (compound of interaction with γ-cyclodextrin according to the method of the present invention or crystallized product F12511) in the dog.

Pharmacokinetic tests on dogs were carried out with an F12511/γ-cyclodextrin interaction compound obtained by this method. Standardized doses of 3 mg/kg were administered to 5 dogs, and the plasma concentration (expressed in ng/ml.h) of F12511 was measured. The results relating to the F12511 obtained after crystallization and drying by a conventional route and those relating to the F12511/γ-cyclodextrin interaction compound obtained by the above-described method of the present invention are shown in the histogram of FIG. 7.

It is found that the administration of doses prepared from the F12511/γ-cyclodextrin interaction compound obtained by the method according to the present invention makes it possible to improve bioavailability in the dog by a factor of 10.

COMPARATIVE EXAMPLE 5

Precipitation and Inclusion in γ-cyclodextrin of Product F12511 Generated by SAS Process/Ethanol An 8 l solution of product F12511 (concentration: 5 g/l) in ethanol is precipitated continuously with the solvent-antisolvent (SAS) process, in the presence of $CO_2$, in a 6 l autoclave equipped with a 4 l basket. The flow rate of the solvent pump is 41.7 ml/min. The temperature and pressure within the autoclave are selected so as to give a $CO_2$ density of 0.8. After approximately 8 l of solution have been precipitated, the injection of the solute and the injection of $CO_2$ are stopped, and the system is let down gently, so as not to liquefy the supercritical fluid.

The 4.3 g of the active substance precipitated in the preceding step are mixed with 25.8 g of γ-cyclodextrin and 10 g of osmosed water, and the mixture is placed in the 4 l Poral basket, which in turn is placed in the 6 l precipitation autoclave.

The autoclave is closed and the system is pressurized with supercritical $CO_2$ so as to give a static pressure of 300 bar, and a temperature of 65° C. within the autoclave.

Letdown is carried out after 16 hours of molecular diffusion.

| Nature of powder | Dissolution (μg/ml) |
| --- | --- |
| F12511 before precipitation | ~15 |
| F12511 precipitated with supercritical $CO_2$ | 80 |
| F12511/γ-cyclodextrin compound after molecular diffusion | 155 |

COMPARATIVE EXAMPLE 6

Precipitation and Inclusion in γ-cyclodextrin of Product F12511 Generated by SAS Process/DMSO A 150 ml solution of product F12511 (concentration: 200 g/l) in DMSO is precipitated continuously with the solvent-antisolvent (SAS) process, in the presence of $CO_2$, in a 2 l autoclave equipped with a 1.37 l basket. The flow rate of the solvent pump is 0.5 ml/min. The temperature and pressure within the autoclave are selected so as to give a $CO_2$ density of 0.9. After approximately 135 ml of solution have been precipitated, the injection of the solute and the injection of $CO_2$ are stopped, and the system is let down gently, so as not to liquefy the supercritical fluid.

The 1 g of the active substance precipitated in the preceding step is mixed with 6 g of γ-cyclodextrin and 2.33 g of osmosed water, and the mixture is placed in the 1.37 l Poral basket, which in turn is placed in the 2 l precipitation autoclave.

The autoclave is closed and the system is pressurized with supercritical $CO_2$ so as to give a static pressure of 300 bar, and a temperature of 100° C. within the autoclave.

Letdown is carried out after 16 hours of molecular diffusion.

| Nature of powder | Dissolution (μg/ml) |
| --- | --- |
| F12511 before precipitation | 5 |
| F12511 precipitated with supercritical $CO_2$ | 57 |
| F12511/γ-cyclodextrin compound after molecular diffusion | 165 |

COMPARATIVE EXAMPLE 7

Inclusion in γ-cyclodextrin of Product F12511 Generated by RESS Process 40 g of product F12511 are placed in a 4 l basket which in turn is placed in a 6 l autoclave. The active substance is extracted with a supercritical mixture of $CO_2$ and ethanol (5% by mass) and the substance is precipitated at 120 bar and 55° C. After 3 hours, the injections of $CO_2$ and of ethanol are stopped.

8.96 g of the active substance precipitated in the preceding step are mixed with 53.76 g of γ-cyclodextrin and 20.87 g of osmosed water, and the mixture is placed in the 4 l Poral basket, which in turn is placed in the 6 l precipitation autoclave.

The autoclave is closed and the system is pressurized with supercritical $CO_2$ so as to give a static pressure of 300 bar, and a temperature of 65° C. within the autoclave.

The autoclave is letdown gently after 16 hours of molecular diffusion.

| Nature of powder | Dissolution (μg/ml) |
| --- | --- |
| F12511 before precipitation | ~10 |
| F12511 precipitated with supercritical $CO_2$ | 8 |
| F12511/γ-cyclodextrin compound after molecular diffusion | 292 |

COMPARATIVE EXAMPLE 8

Inclusion in γ-cyclodextrin of Product L0081 by Stirred Molecular Diffusion 4.0 g of product L0081, 24.0 g of γ-cyclodextrin, and 9.3 g of water are mixed.

The resulting mixture is placed at the bottom of a 1-liter stirred autoclave. The autoclave is hermetically closed and then pressurized to 300 bar with $CO_2$ in the supercritical state. The temperature was set at 50° C.±10° C. Stirring is commenced (400 rpm), and the pressure and temperature are maintained overnight. After one night the heating and stirring are switched off and the autoclave is gently depressurized. All of the powder is recovered, and dissolution tests are conducted, and are compared with those on the powder obtained, under the same conditions but without stirring:

| Nature of powder | Dissolution (μg/ml) |
| --- | --- |
| L0081/γ-cyclodextrin compound obtained by molecular diffusion without stirring | 124 |

-continued

| Nature of powder | Dissolution (µg/ml) |
|---|---|
| L0081/γ-cyclodextrin compound obtained by molecular diffusion with stirring | 334 |

Summary of Results

The table below summarizes the different methods employed and also the corresponding dissolution results, and permits the deduction therefrom of the method most suitable for the manufacture of F12511 product with high dissolution in aqueous medium:

| Method | Comp. Ex. 1 | Comp. Ex. 2 | Comp. Ex. 3 | Ex. 4 | Ex. 4 | Comp. Ex. 5 | Comp. Ex. 5 |
|---|---|---|---|---|---|---|---|
| Precipitation * by RESS | | X | | | | | |
| Precipitation * by SAS/DMSO | X | | | | | | |
| Coprecipitation ** by SAS/DMSO | | | X | X | X | | |
| Precipitation * by SAS/EtOH | | | | | | X | X |
| Conventional crystallization | | | | | | | |
| Stirred molecular diffusion | | | | X | X | | X |
| Non-stirred moleculardiffusion | | | | | | | |
| Washing | X | | X | | X | | |
| Dissolution (µg/ml) | 62 | 76 | 100 | 440 | 662 | 80 | 155 |

| Method | Comp. Ex. 6 | Comp. Ex. 6 | Comp. Ex. 7 | Comp. Ex. 7 | Comp. Ex. 8 | Comp. Ex. 8 |
|---|---|---|---|---|---|---|
| Precipitation * by RESS | | | X | X | | |
| Precipitation * by SAS/DMSO | X | X | | | | |
| Coprecipitation ** by SAS/DMSO | | | | | | |
| Precipitation * by SAS/EtOH | | | | | | |
| Conventional crystallization | | | | | X | X |
| Stirred molecular diffusion | | | | | | X |
| Non-stirred molecular diffusion | | X | | X | X | |
| Washing | X | | | | | |
| Dissolution (µg /ml) | 57 | 165 | 8 | 292 | 124 | 334 |

* Precipitation of product F12511 alone
** Coprecipitation of a solution of product F12511 and γ-cyclodextrin In light of these results it is clear that the method which allows the greatest dissolution of product F12511 in an aqueous medium to be obtained is the method combining the steps of generating product F12511 using supercritical fluid, advantageously by coprecipitation of product F12511 and γ-cyclodextrin, molecular diffusion in static mode, advantageously with stirring, and washing.

Comparative Tests 9:

To validate the fact that it is indeed the method as a whole that allows us to obtain the end results, and not one of the intermediate steps, we carried out dissolution tests as described above on various mixtures and obtained the following results:

| | Before diffusion | After diffusion |
|---|---|---|
| F12511/γ-cyclodextrin Crude powders Physical mixture | 19 µg/ml | 142 µg/ml |
| F12511/γ-cyclodextrin Powders crystallized by SAS Separately Physical mixture | 69 µg/ml | 150 µg/ml |

| | Before diffusion | After diffusion |
|---|---|---|
| F12511/γ-cyclodextrin Cocrystallized powders | 100 µg/ml | 671 µg/ml |

Testing with Other Active Substances, Other Supports and Other Solvents:

In order to validate the results obtained with F12511, different molecules belonging to different therapeutic classes were tested:

| Active principle | Therapeutic class |
|---|---|
| Ketoprofen | Antiinflammatory |
| Omeprazole | Antiulcerative |
| Simvastatin | Hypocholesterolemic |
| Terfenadine | Antihistamine |

Manufacturing Conditions for the Powders Studied:

The following method is applied for each of the powders studied:
- Dissolution of the active principle and cyclodextrin studied in the solvent.
- Intimate mixing of the active principle and cyclodextrin studied by SAS in the presence of supercritical $CO_2$.
- Drying of the powder obtained
- Taking of a sample (in certain cases),
- Mixing of the powder with osmosed water, then inclusion under $CO_2$ at supercritical pressure.
- Drying of the powder obtained,
- Taking of a sample.

The tests on these new molecules were carried out different solvents and different types of support. The various tests carried out are summarized in the table below:

| Active principle | Cyclodextrin | Solvent | Concentration of active principle (g/l) |
|---|---|---|---|
| Ketoprofen | β | DMSO | 25 |
| Omeprazole | γ | DMSO | 33 |
|  | γ | DMF | 30 |
| Simvastatin | γ | DMSO | 25 |
|  | γ | DMF | 15 |
| Terfenadine | β | DMSO | 16 |
|  | β | DMF | 30 |
|  | Methyl-P | ethanol | 8 |

EXAMPLE 10 ketoprofen/β-cyclodextrin/DMSO

Operating Parameters:

| Mixing | |
|---|---|
| Time (h) | 2 |
| Pressure (MPa) | 15 |
| Temperature (K) | 313 |
| Molar ratio $CO_2$/solvent | 400 |
| Flow rate of the solution (ml/min) | 1 |
| Drying | |
| Time (h) | 1 |
| Pressure (MPa) | 15 |
| Temperature (K) | 313 |
| Flow rate of $CO_2$ (kg/h) | 15 |
| Inclusion | |
| Addition of water (% total mass) | 25 |
| Time (h) | 16 |
| Pressure (MPa) | 15 |
| Temperature (K) | 333 |

Powder Analysis Protocol: Dissolution Test

Operating conditions:

UV analysis at a wavelength of 260 nm.

Control Solution:

Prepare a standard solution in $H_2O$. Ensure that an absorbance<2 is maintained.

Execution of the Analysis:

Prepare 50 ml of a solution of ketoprofen in water by introducing an amount of powder equivalent to 50 mg of active principle.

Dissolve the powder with magnetic stirring using a stirrer bar in a waterbath at 37±0.5° C.

Withdraw 2 ml of this suspension after 2 hours of stirring and filter it on a 0.45 μm Gelman GHP filter. Carry out the UV analysis, ensuring that the absorbance is less than 2. If it is not, carry out dilution.

Result Obtained:

After 2 hours of dissolution the concentrations (μg/ml) measured are as follows:

| Active principle alone | Powder after whole method |
|---|---|
| 333 | 923 |

EXAMPLE 11 omeprazole/γ-cyclodextrin/DMSO

Operating Parameters:

| Mixing | |
|---|---|
| Time (h) | 2 |
| Pressure (MPa) | 15 |
| Temperature (K) | 313 |
| Molar ratio $CO_2$/solvent | 400 |
| Flow rate of the solution (ml/min) | 1 |
| Drying | |
| Time (h) | 1 |
| Pressure (MPa) | 15 |
| Temperature (K) | 313 |
| Flow rate of $CO_2$ (kg/h) | 15 |
| Inclusion | |
| Addition of water (% total mass) | 25 |
| Time (h) | 16 |
| Pressure (MPa) | 15 |
| Temperature (K) | 333 |

Powder Analysis Protocol: Dissolution Test

Operating Conditions:

UV analysis at a wavelength of 296 nm.

Control Solution:

Prepare a standard solution in 1% (m/v) sodium lauryl sulfate in $H_2O$. Ensure that an absorbance<2 is maintained.

Execution of the Analysis:

Prepare 50 ml of a solution of omeprazole in water by introducing an amount of powder equivalent to 50 mg of active principle.

Dissolve the powder with magnetic stirring using a stirrer bar in a waterbath at 37±0.5° C.

Withdraw 2 ml of this suspension after 2 hours of stirring and filter it on a 0.45 μm Gelman GHP filter. Carry out the UV analysis, ensuring that the absorbance is less than 2. If it is not, carry out dilution.

Results Obtained:

After 2 hours of dissolution the concentrations (μg/ml) measured are as follows:

| Active principle alone | Powder after whole method |
|---|---|
| 91 | 129 |

EXAMPLE 12 omeprazole/γ-cyclodextrin/DMF

Operating Parameters

| Mixing | |
|---|---|
| Time (h) | 2 |
| Pressure (MPa) | 15 |
| Temperature (K) | 313 |
| Molar ratio $CO_2$/solvent | 400 |
| Flow rate of the solution (ml/min) | 1 |
| Drying | |
| Time (h) | 1 |
| Pressure (MPa) | 15 |
| Temperature (K) | 313 |
| Flow rate of $CO_2$ (kg/h) | 15 |
| Inclusion | |
| Addition of water (% total mass) | 25 |
| Time (h) | 16 |
| Pressure (MPa) | 15 |
| Temperature (K) | 333 |

Powder Analysis Protocol: Dissolution Test

Operating Conditions:
 UV analysis at a wavelength of 296 nm.

Control Solution:
 Prepare a standard solution in 1% (m/v) sodium lauryl sulfate in $H_2O$. Ensure that an absorbance<2 is maintained.

Execution of the Analysis:
 Prepare 50 ml of a solution of omeprazole in water by introducing an amount of powder equivalent to 50 mg of active principle.
 Dissolve the powder with magnetic stirring using a stirrer bar in a waterbath at 37±0.5° C.
 Withdraw 2 ml of this suspension after 2 hours of stirring and filter it on a 0.45 μm Gelman GHP filter. Carry out the UV analysis, ensuring that the absorbance is less than 2. If it is not, carry out dilution.

Results Obtained:
 After 2 hours of dissolution the concentrations (μg/ml) measured are as follows:

| Active principle alone | Powder after whole method |
|---|---|
| 91 | 216 |

EXAMPLE 13 simvastatin/γ-cyclodextrin/DMSO

Operating Parameters.

| Mixing | |
|---|---|
| Time (h) | 2 |
| Pressure (MPa) | 15 |
| Temperature (K) | 313 |
| Molar ratio $CO_2$/solvent | 400 |
| Flow rate of the solution (ml/min) | 1 |
| Drying | |
| Time (h) | 1 |
| Pressure (MPa) | 15 |
| Temperature (K) | 313 |
| Flow rate of $CO_2$(kg/h) | 15 |
| Inclusion | |
| Addition of water (% total mass) | 25 |
| Time (h) | 16 |
| Pressure (MPa) | 15 |
| Temperature (K) | 333 |

Powder Analysis Protocol: Dissolution Test

Operating Conditions:
 UV analysis at a wavelength of 248 nm.

Control Solution:
 Prepare a standard solution in 1% (m/v) sodium lauryl sulfate in $H_2O$. Ensure that an absorbance<2 is maintained.

Execution of the Analysis:
 Prepare 50 ml of a solution of simvastatin in water by introducing an amount of powder equivalent to 50 mg of active principle.
 Dissolve the powder with magnetic stirring using a stirrer bar in a waterbath at 37±0.5° C.
 Withdraw 2 ml of this suspension after 2 hours of stirring and filter it on a 0.45 μm Gelman GHP filter. Carry out the UV analysis, ensuring that the absorbance is less than 2. If it is not, carry out dilution.

Result Obtained:
 After 2 hours of dissolution the concentrations (μg/ml) measured are as follows:

| Active principle alone | Powder after mixing | Powder after whole method |
|---|---|---|
| <1 | 23 | 300 |

EXAMPLE 14 simvastatin/γ-cyclodextrin/DMF

Operating Parameters:

| Mixing | |
|---|---|
| Time (h) | 2 |
| Pressure (MPa) | 15 |
| Temperature (K) | 313 |
| Molar ratio $CO_2$/solvent | 400 |
| Flow rate of the solution (ml/min) | 1 |
| Drying | |
| Time (h) | 1 |
| Pressure (MPa) | 15 |
| Temperature (K) | 313 |
| Flow rate of $CO_2$ (kg/h) | 15 |

-continued

| Inclusion | |
|---|---|
| Addition of water (% total mass) | 25 |
| Time (h) | 16 |
| Pressure (MPa) | 15 |
| Temperature (K) | 333 |

Powder Analysis Protocol: Dissolution Test

Operating Conditions:
UV analysis at a wavelength of 248 nm.

Control Solution:
Prepare a standard solution in 1% (m/v) sodium lauryl sulfate in $H_2O$. Ensure that an absorbance<2 is maintained.

Execution of the Analysis:
Prepare 50 ml of a solution of simvastatin in water by introducing an amount of powder equivalent to 50 mg of active principle.
Dissolve the powder with magnetic stirring using a stirrer bar in a waterbath at 37±0.5° C.
Withdraw 2 ml of this suspension after 2 hours of stirring and filter it on a 0.45 µm Gelman GHP filter. Carry out the UV analysis, ensuring that the absorbance is less than 2. If it is not, carry out dilution.

Result Obtained:
After 2 hours of dissolution the concentrations (µg/ml) measured are as follows:

| Active principle alone | Powder after mixing | Powder after whole method |
|---|---|---|
| <1 | 13 | 212 |

EXAMPLE 15 terfenadine/β-cyclodextrin/DMSO

Operating Parameters:

| Mixing | |
|---|---|
| Time (h) | 2 |
| Pressure (MPa) | 15 |
| Temperature (K) | 313 |
| Molar ratio $CO_2$/solvent | 400 |
| Flow rate of the solution (ml/min) | 1 to 1.2 |
| Drying | |
| Time (h) | 1 |
| Pressure (MPa) | 15 |
| Temperature (K) | 313 |
| Flow rate of $CO_2$ (kg/h) | 15 |
| Inclusion | |
| Addition of water (% total mass) | 25 |
| Time (h) | 16 |
| Pressure (MPa) | 15 |
| Temperature (K) | 333 |

Powder Analysis Protocol: Dissolution Test

Operating Conditions:
UV analysis at a wavelength of 259 nm.

Control Solution:
Prepare a standard solution in 1% (m/v) sodium lauryl sulfate in $H_2O$. Ensure that an absorbance<2 is maintained.

Execution of the Analysis:
Prepare 50 ml of a solution of terfenadine in water by introducing an amount of powder equivalent to 50 mg of active principle.
Dissolve the powder with magnetic stirring using a stirrer bar in a waterbath at 37±0.5° C.
Withdraw 2 ml of this suspension after 2 hours of stirring and filter it on a 0.45 µm Gelman GHP filter. Carry out the UV analysis, ensuring that the absorbance is less than 2. If it is not, carry out dilution.

Result Obtained:
After 2 hours of dissolution the concentrations (µg/ml) measured are as follows:

| Active principle alone | Powder after mixing | Powder after whole method |
|---|---|---|
| <1 | 290 | 990 |

EXAMPLE 16 terfenadine/β-cyclodextrin/DMF

Operating Parameters:

| Mixing | |
|---|---|
| Time (h) | 2 |
| Pressure (MPa) | 15 |
| Temperature (K) | 313 |
| Molar ratio $CO_2$/solvent | 400 |
| Flow rate of the solution (ml/min) | 1 to 1.2 |
| Drying | |
| Time (h) | 1 |
| Pressure (MPa) | 15 |
| Temperature (K) | 313 |
| Flow rate of $CO_2$ (kg/h) | 15 |
| Inclusion | |
| Addition of water (% total mass) | 25 |
| Time (h) | 16 |
| Pressure (MPa) | 15 |
| Temperature (K) | 333 |

Powder Analysis Protocol: Dissolution Test

Operating Conditions:
UV analysis at a wavelength of 259 nm.

Control Solution:
Prepare a standard solution in 1% (m/v) sodium lauryl sulfate in $H_2O$. Ensure that an absorbance<2 is maintained.

Execution of the Analysis:
Prepare 50 ml of a solution of terfenadine in water by introducing an amount of powder equivalent to 50 mg of active principle.
Dissolve the powder with magnetic stirring using a stirrer bar in a waterbath at 37±0.5° C.

Withdraw 2 ml of this suspension after 2 hours of stirring and filter it on a 0.45 μm Gelman GHP filter. Carry out the UV analysis, ensuring that the absorbance is less than 2. If it is not, carry out dilution.

Result Obtained:

After 2 hours of dissolution the concentrations (μg/ml) measured are as follows:

| Active principle alone | Powder after whole method |
|---|---|
| <1 | 323 |

EXAMPLE 17 terfenadine/methyl-β-cyclodextrin/ethanol

Operating Parameters:

| Mixing | |
|---|---|
| Time (h) | 2 |
| Pressure (MPa) | 15 |
| Temperature (K) | 313 |

-continued

| Molar ratio $CO_2$/solvent | 400 |
|---|---|
| Flow rate of the solution (ml/min) | 1 to 1.2 |
| Drying | |
| Time (h) | 1 |
| Pressure (MPa) | 15 |
| Temperature (K) | 313 |
| Flow rate of $CO_2$ (kg/h) | 15 |
| Inclusion | |
| Addition of water (% total mass) | 25 |
| Time (h) | 16 |
| Pressure (MPa) | 15 |
| Temperature (K) | 333 |

Powder Analysis Protocol: Dissolution Test

Operating Conditions:

UV analysis at a wavelength of 259 nm.

Control Solution:

Prepare a standard solution in 1% (m/v) sodium lauryl sulfate in $H_2O$. Ensure that an absorbance<2 is maintained.

Execution of the Analysis:

Prepare 50 ml of a solution of terfenadine in water by introducing an amount of powder equivalent to 50 mg of active principle.

Dissolve the powder with magnetic stirring using a stirrer bar in a waterbath at 37±0.5° C.

Withdraw 2 ml of this suspension after 2 hours of stirring and filter it on a 0.45 μm Gelman GHP filter. Carry out the UV analysis, ensuring that the absorbance is less than 2. If it is not, carry out dilution.

Result Obtained:

After 2 hours of dissolution the concentrations (μg/ml) measured are as follows:

| Active principle alone | Powder after mixing | Powder after whole method |
|---|---|---|
| <1 | 420 | 552 |

The table below collates the various dissolution results (μg/ml) obtained for all of the molecules tested:

| | | | Dissolution of 2 hours | | |
|---|---|---|---|---|---|
| MOLECULE | SOLVENT | CYCLO | Active principle alone | Powder after cocrystallization | Powder after whole method |
| F12511 | DMSO | β | 12 | 100 | 662 |
| Ketoprofen | DMSO | β | 333 | X | 923 |
| Omeprazole | DMSO | γ | 91 | X | 129 |
|  | DMF | γ | 91 | X | 216 |
| Simvastatin | DMSO | γ | <1 | 23 | 300 |
|  | DMF | γ | <1 | 13 | 212 |
| Terfenadine | DMSO | β | <1 | 290 | 990 |
|  | DMF | β | <1 | X | 323 |
|  | ETHANOL | Methyl-β | <1 | 420 | 552 |

NB: the cases indicating X correspond to samples not taken.

In light of these results it is clear that the method which allows the greatest dissolution of the active principles in an aqueous medium to be obtained is that combining the steps of mixing active principle and porous support, advantageously cyclodextrin, molecular diffusion, and drying. This property is observed for various active principles, various types of cyclodextrins, and various solvents.

The invention claimed is:

1. A method for preparing a complex of an active substance of low solubility in an aqueous medium with a porous support, comprising the following steps:
   generating the active substance of low solubility in an aqueous medium by supercritical fluid,
   (a) mixing the active substance generated by supercritical fluid and a defined amount of the porous support,
   (b) implementing a step of molecular diffusion in order to obtain a complex by contacting in static mode a supercritical fluid with the mixture obtained in step (a) for a time required to improve dissolution in an aqueous medium of the mixture obtained in step (a),
   (c) washing the complex obtained in step (b) with a flow of supercritical fluid,
   (d) recovering particles of the complex formed in step (c).

2. The method according to claim 1, wherein the supercritical fluid is $CO_2$.

3. The method according to claim 1, wherein the active substance is selected from the group consisting of anilide derivatives, epipodophyllotoxin derivatives, piroxicam, valeric acid, octanoic acid, laurie acid, and stearic acid.

4. The method according to claim 1, wherein the porous support is selected from the group consisting of cyclodextrins and a mixture thereof.

5. The method according to claim 1, wherein the implementing step of molecular diffusion is carried out with stirring.

6. The method according to claim 1, wherein the implementing step of molecular diffusion is carried out in the presence of a diffusion agent.

7. The method according to claim 6, wherein the diffusion agent is selected from the group consisting of alcohol, water with or without surfactant, and mixtures thereof.

8. The method according to claim 1, wherein during the implementing step a pressure of the supercritical fluid is between 10 MPa and 40 MPa and a temperature is between 0 and 120° C.

9. The method according to claim 1, wherein each of the steps of the method is implemented in a closed reactor.

10. The method according to claim 1, wherein the method is carried out continuously.

11. The method according to claim 1, wherein the porous support is generated by supercritical fluid and wherein the mixing step consists in a coprecipitation of the active substance and of the porous support by the solvent anti-solvent (SAS) process.

12. The method according to claim 1, wherein the active substance, before being used in the mixing step, is generated by precipitation in accordance with the SAS process and wherein the porous support used in the mixing step is in solid form.

13. The method according to claim 1, wherein the active substance before being used in the mixing step is generated by precipitation in accordance with the rapid expansion of supercritical solutions (RESS) process and wherein the porous support used in the mixing step is in solid form.

14. The method according to claim 1, 12 or 13, wherein the mixing step consists in the precipitation of the active substance on the porous support by the SAS process.

15. The method according to claim 1, 12 or 13, wherein the mixing step consists in the precipitation of the active substance on the porous support by the RESS process.

* * * * *